(12) United States Patent
Lee et al.

(10) Patent No.: US 10,006,893 B2
(45) Date of Patent: Jun. 26, 2018

(54) METHOD FOR DETECTING CRYSTAL GRAIN BOUNDARIES OF GRAPHEME AND DEVICE USING METHOD

(71) Applicant: Hanwha Techwin Co., Ltd., Changwon-si (KR)

(72) Inventors: Eunkyu Lee, Changwon-si (KR); Jonghyuk Yoon, Changwon-si (KR)

(73) Assignee: Hanwha Techwin Co., Ltd., Changwon-si (KR)

( * ) Notice: Subject to any disclaimer, the term of this patent is extended or adjusted under 35 U.S.C. 154(b) by 42 days.

(21) Appl. No.: 14/771,834

(22) PCT Filed: Nov. 29, 2013

(86) PCT No.: PCT/KR2013/010946
§ 371 (c)(1),
(2) Date: Sep. 1, 2015

(87) PCT Pub. No.: WO2014/137057
PCT Pub. Date: Sep. 12, 2014

(65) Prior Publication Data
US 2016/0025693 A1 Jan. 28, 2016

(30) Foreign Application Priority Data
Mar. 6, 2013 (KR) .................. 10-2013-0023945

(51) Int. Cl.
| | | |
|---|---|---|
| G01N 31/10 | (2006.01) | |
| C01B 31/02 | (2006.01) | |
| C01B 31/04 | (2006.01) | |
| G01N 13/00 | (2006.01) | |
| G01N 21/75 | (2006.01) | |
| B82Y 30/00 | (2011.01) | |
| C01B 32/182 | (2017.01) | |

(52) U.S. Cl.
CPC .............. *G01N 31/10* (2013.01); *B82Y 30/00* (2013.01); *C01B 32/182* (2017.08); *G01N 21/75* (2013.01)

(58) Field of Classification Search
CPC ........ G01N 31/10; G01N 21/75; B82Y 30/00; C01B 31/0438
See application file for complete search history.

(56) References Cited

U.S. PATENT DOCUMENTS

2014/0183160 A1* 7/2014 Chiba .................... C01B 31/02
216/36

FOREIGN PATENT DOCUMENTS

| CN | 102229426 B | 12/2012 | |
|---|---|---|---|
| JP | 2008-214672 A | 9/2008 | |
| KR | 10-2010-0112726 A | 10/2010 | |
| KR | 10-2012-0046601 A | 5/2012 | |
| WO | WO 2012165051 A1 * | 12/2012 | ............... C22C 9/00 |

OTHER PUBLICATIONS

Jia, Chuancheng, et al. "Direct optical characterization of graphene growth and domains on growth substrates." Scientific reports 2 (2012): 707.*

(Continued)

*Primary Examiner* — Robert Eom
(74) *Attorney, Agent, or Firm* — Sughrue Mion, PLLC

(57) ABSTRACT

Provided are a method of detecting a grain boundary of graphene and a device using the same.

3 Claims, 4 Drawing Sheets

(56) References Cited

OTHER PUBLICATIONS

Bae, Sukang, et al. "Roll-to-roll production of 30-inch graphene films for transparent electrodes." Nature nanotechnology 5.8 (2010): 574-578.*

Communication dated Jul. 20, 2016, issued by the State Intellectual Property Office of P.R. China in counterpart Chinese application No. 201380074314.

Duong et al., "Probing graphene grain boundaries with optical microscopy", Nature, Oct. 11, 2012, 7 pages total, vol. 490, Macmillan Publishers Limited.

Kim et al., "Direct visualization of large-area graphene domains and boundaries by optical birefringency", Nature Nanotechnology, Jan. 2012, 7 pages total, vol. 7, Macmillan Publishers Limited.

Li et. al., "Large-Area Synthesis of High-Quality and Uniform Graphene Films on Copper Foils", Science AAAS 324, Jun. 5, 2009, 5 pages total, District of Columbia, USA.

Chen et al., "Oxidation resistance of graphene-coated Cu and Cu/Ni alloy", Feb. 22, 2011, 18 pages total, China, USA.

International Search Report dated Feb. 10, 2014 issued by International Searching Authority in counterpart International Application No. PCT/KR2013/010946.

Written Opinion dated Feb. 10, 2014 issued by International Searching Authority in counterpart International Application No. PCT/KR2013/010946.

Communication dated Mar. 6, 2017, from the State Intellectual Property Office of People's Republic of China in counterpart Application No. 201380074314.X.

* cited by examiner

GRAPHENE UNIT GRAIN

METHOD FOR DETECTING CRYSTAL GRAIN BOUNDARIES OF GRAPHEME AND DEVICE USING METHOD

TECHNICAL FIELD

The present invention relates to a method of detecting a grain boundary of grapheme and a device using the method.

The present invention relates to a national research project having details as follows: Project Number: 10033309, Research Project: Industrial source technology development, Managing Department: Korea Institute of Machinery and Metal, and Project Title: "Technology development for large-area transcription and continuous production system for flexible nano-thin films."

BACKGROUND ART

Novel materials for use in various electronic devices, such as display devices and solar batteries, have been actively developed. In particular, research into novel materials that can replace indium tin oxide (ITO), which is generally used in forming a transparent electrode for electronic devices, has been actively performed. Among such novel materials, a carbon-containing material, such as carbon nanotubes, diamond, graphite, grapheme, or the like, is where the research is focused.

In particular, graphene has excellent electric conductivity and transparency, and due to such features, various methods for preparing graphene have been developed. Methods for preparing graphene can be largely classified into a mechanical method and a chemical method. An example of the mechanical method is separating graphene from a graphite sample by using a Scotch tape. This method does not damage the surface of graphene but is not suitable for a large-area graphene. An example of the chemical method is a chemical vapor deposition (CVD). According to CVD, a vaporous carbon supplier is placed in a container with catalytic metal located therein, and the container is heated and then cooled, thereby growing a graphene sheet on the surface of the catalytic metal.

Graphene prepared by CVD has grain boundaries which are formed by connecting several islands in an initial growth stage. Grain boundaries of graphene determine mobility properties associated with performance of a device. However, since grain boundaries of graphene can be identifiable under transmission electron microscope (TEM) or scanning tunneling microscope (STM), it is not easy to detect the grain boundaries of graphene.

DETAILED DESCRIPTION OF THE INVENTION

Technical Problem

Embodiments of the present invention provide a method of detecting a grain boundary of graphene and a device using the method.

Technical Solution

An embodiment of the present invention provides a method of detecting a grain boundary of graphene, the method including oxidizing a catalytic metal by reacting a stack of the catalytic metal and graphene with an oxidizing solution.

Another embodiment of the present invention provides a device for detecting a grain boundary of graphene, the device including a reactor oxidizing a catalytic metal by reacting a stack of the catalytic metal and graphene with an oxidizing solution.

Advantageous Effects of the Invention

According to embodiments of the present invention, in the case of a large-area graphene, a grain boundary of graphene can be easily detectable under optical microscope.

BEST MODE OF THE INVENTION

Figure 1:
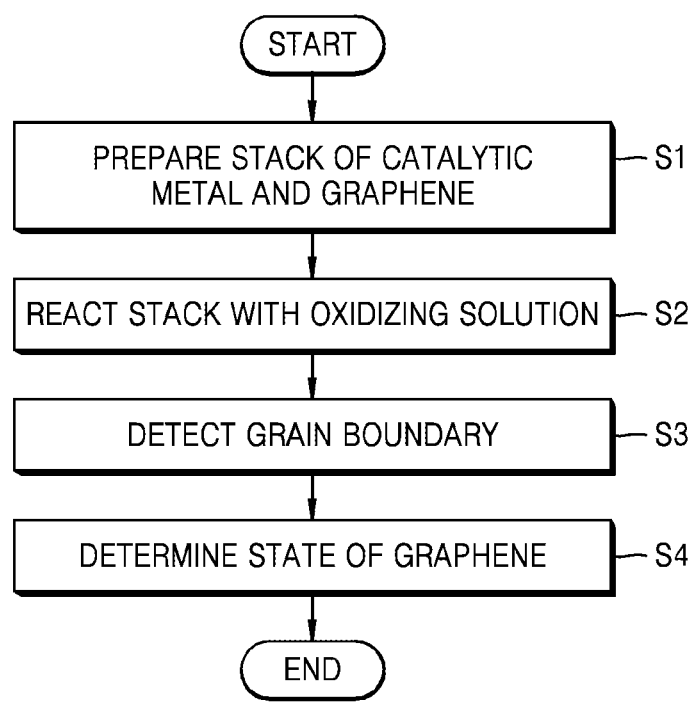
FIG. 1 is a flowchart schematically illustrating a method of detecting a grain boundary of graphene, according to an embodiment of the present invention.

An embodiment of the present invention provides a method of detecting a grain boundary of graphene, the method including oxidizing a catalytic metal by reacting a stack of the catalytic metal and graphene with an oxidizing solution.

The oxidizing solution may be 5 to 100 wt % of an aqueous hydrogen peroxide solution.

The oxidizing solution may be used in an amount of 0.001 to 1 L based on 1 m² of a unit area of the stack of the catalytic metal and graphene.

The catalytic metal may be at least one selected from copper (Cu), nickel (Ni), cobalt (Co), iron (Fe), platinum (Pt), gold (Au), silver (Ag), aluminum (Al), chromium (Cr), magnesium (Mg), manganese (Mn), molybdenum (Mo), rhodium (Rh), silicon (Si), tantalum (Ta), titanium (Ti), tungsten (W), uranium (U), vanadium (V), palladium (Pd), yttrium (Y), zirconium (Zr), germanium (Ge), and an alloy thereof.

The catalytic metal may be oxidized for 1 sec. to 10 min.

Another embodiment of the present invention provides a device for detecting a grain boundary of graphene, the device including a reactor oxidizing a catalytic metal by reacting a stack of the catalytic metal and graphene with an oxidizing solution.

The device may further include a detector for detecting a grain boundary of graphene by using an optical microscope.

The reactor and the detector may be connected to each other in series.

The reactor may further include a plurality of rollers transporting the stack of the catalytic metal and graphene.

The device may further include a determination unit connected to the detector.

Mode of the Invention

As the invention allows for various changes and numerous embodiments, exemplary embodiments will be illustrated in the drawings and described in detail in the written description. However, this is not intended to limit the present invention to particular modes of practice, and it is to be appreciated that all changes, equivalents, and substitutes that do not depart from the spirit and technical scope of the present invention are encompassed in the present invention. In the description of the present invention, certain detailed explanations of the related art are omitted when it is deemed that they may unnecessarily obscure the essence of the invention.

While such terms as "first," "second," etc., may be used to describe various components, such components must not be limited to the above terms. The above terms are used only to distinguish one component from another.

It will be understood that when a layer, a film, a region, a plate, or the like is referred to as being "formed on" another layer, film, region, or plate, it can be directly or indirectly formed on the other layer, film, region, or plate. That is, for example, intervening layers, films, regions, or plates may be present Hereinafter, embodiments of the present invention will be described below with reference to the drawings, and in this case, substantially identical or corresponding elements will be denoted with the same reference numeral and description thereof will be presented once, and later, omitted. In the drawings, the thicknesses of layers and regions are exaggerated for clarity Hereinafter, a method of detecting a grain boundary of graphene and a system using the method, according to embodiments of the present invention, will be described below.

The term "graphene" used herein refers to a 2-dimensional film-like structure (in general, sp2 bond) consisting of a plurality of carbon atoms that are covalently bonded each other. Carbon atoms constituting graphene form a six-membered ring as a repeating unit. Graphene may further include carbon atoms that form a 5 membered-ring and/or 7 membered-ring along a grain boundary in a graphene layer. Graphene may have a defect in the form of vacancy, which is where the bond structure of an atom unit is absent or discontinuous. Graphene may be a single layer. However, in some embodiments, such a single layer may be stacked two or more times, thereby forming a multilayer. Graphene may have a thickness of 100 nm or less.

The term "a grain boundary of graphene" refers to a boundary of single crystals where single crystals meet and chemically bond or simply, physically contact or are adjacent to their neighboring crystals, when graphene grows into the single crystals on a catalytic metal from a plurality of growth nucli to form a continuous layer consisting of a plurality of crystals.

The term "a stack" refers to a plurality of layers including graphene, and according to steps of the method of preparing graphene according to an embodiment of the present invention, the stack may refer to a stack that includes, in addition to graphene, at least one selected from a catalytic metal and an oxidized catalytic metal.

An aspect of the present invention provides a method of detecting a grain boundary of graphene, the method including oxidizing a catalytic metal by reacting a stack of the catalytic metal and graphene with an oxidizing solution.

Typically, a grain boundary of graphene has a width in a nano unit, and accordingly, is not identifiable under optical microscope. The method of detecting a grain boundary of graphene according to an embodiment of the present invention enables the grain boundary of graphene to be detectable by oxidizing the catalytic metal. The catalytic metal is oxidized by an oxidizing material, for example, an oxygen radical (O.) and/or a hydroxy radical (OH.) present in a hydrogen peroxide solution, and once the catalytic metal is oxidized, the catalytic metal has a volume greater than that before the oxidization, and accordingly, a grain boundary of the oxidized catalytic metal is identifiable under optical microscope.

The oxygen radical and/or the hydroxy radical may diffuse into a 7 membered-ring portion in graphene. The diffused oxygen radical and/or hydroxy radical may reach a portion of the surface of the catalytic metal, the portion contacting graphene. The diffused oxygen radical and/or hydroxy radical oxidizes the catalytic metal along the shape of the grain boundary of graphene, thereby allowing the grain boundary of graphene to be indirectly identifiable under optical microscope. When the grain boundary of graphene has a 5 membered-ring or a 7 membered-ring, or a vacancy defect, the corresponding portion thereof may allow hydrogen peroxide passes therethrough, and in this case, the formation of radicals due to the catalytic metal may be more promoted, thereby facilitating an oxidation reaction.

When the stack of the catalytic metal and graphene is reacted with the oxidizing solution, damage of the graphene done by the oxidizing solution is small. Also, since the oxidizing solution selectively oxidizes only the catalytic metal, a surface resistance of a graphene layer may not be increased. Accordingly, graphene that is treated by using the method of detecting a grain boundary of graphene according to embodiments of the present invention may have a surface resistance of 30 to 1000 $\Omega$/sqr, for example, 100 to 500 $\Omega$/sqr.

In addition, since the oxidizing solution, for example, an aqueous hydrogen peroxide solution is used for the reaction, the detection method is simple and is applicable to a large-area graphene. Furthermore, since the oxidizing solution used in the detection method is inexpensive, the use of, for example, an aqueous hydrogen peroxide solution may contribute to a decrease in manufacturing costs.

The oxidizing solution may be may be 5 to 100 wt % of the aqueous hydrogen peroxide solution. For example, the oxidizing solution may be 5 to 40 wt % of the aqueous hydrogen peroxide solution. When the amount of the aqueous hydrogen peroxide solution is within these ranges, oxygen and/or hydroxy radicals may be supplied in an amount sufficient to oxidize the catalytic metal while graphene is not damaged.

In some embodiments, the oxidizing solution may include water as a solvent. However, the oxidizing solution is not limited thereto. The oxidizing solution may further include other solvents that are compliable with water.

In some embodiments, the oxidizing solution may further include an additive. However, the oxidizing solution is not limited thereto. For example, the oxidizing solution may include a dispersant, a preservative stabilizer, a stabilizer, or a combination thereof. An amount of the additive may be in a range of 1 to 15 wt % based on a total weight of the oxidizing solution.

The oxidizing of the catalytic metal may be performed by using any method that oxidizes the catalytic metal. For example, the stack of the catalytic metal and graphene may be impregnated with the oxidizing solution, or the oxidizing solution may be coated on or sprayed onto the stack of the catalytic metal and graphene.

An amount of the oxidizing solution may be in a range of 0.001 to 1 L based on 1 $m^2$ of a unit area of the stack of the catalytic metal and graphene, but is not limited thereto. For example, the amount of the oxidizing solution may be in a range of 0.3 to 0.7 L based on 1 $m^2$ of a unit area of 1 $m^2$ of the stack of catalytic metal and graphene. Within these ranges, the oxidizing solution may provide hydroxy radicals enough to oxidize the catalytic metal.

The oxidizing of the catalytic metal may be performed for 1 sec. to 10 min. For example, the oxidizing of the catalytic metal may be performed for 10 sec. to 5 min. Within these ranges, the catalytic metal may sufficiently oxidize a grain boundary of the catalytic metal, thereby allowing the grain boundary of graphene to be detectable under optical microscope.

The catalytic metal may be any material that oxidizes an oxygen radical and/or a hydroxy radical while growing graphene. For example, the catalytic metal may be at least one selected from copper (Cu), nickel (Ni), cobalt (Co), iron (Fe), platinum (Pt), gold (Au), silver (Ag), aluminum (Al), chromium (Cr), magnesium (Mg), manganese (Mn), molybdenum (Mo), rhodium (Rh), silicon (Si), tantalum (Ta), titanium (Ti), tungsten (W), uranium (U), vanadium (V), palladium (Pd), yttrium (Y), zirconium (Zr), germanium (Ge), and an alloy thereof, but is not limited thereto. For example, the catalytic metal may be at least one selected from silver copper (Cu), nickel (Ni), and an alloy thereof, but is not limited thereto.

The catalytic metal may be where graphene grows. The catalytic metal is not limited as long as graphene grows thereon. For example, the catalytic metal may be a sheet, a substrate, or a film.

In some embodiments, after the oxidizing of the catalytic metal, the detection method may further include detecting a grain boundary of graphene by using an optical microscope. However, the detection method may not be limited thereto. The detecting of the grain boundary of graphene is not limited as long as a closed curve of the grain boundary is detectable.

In some embodiments, after the detecting of the grain boundary of graphene, the detection method may further include determining the state of graphene. However, the detection method is not limited thereto. In the detecting of the grain boundary of graphene, a closed curve of the grain boundary of graphene is detected, and a width, shape, and/or inner area distribution of the closed curve may be identified to determine the state of graphene. That is, it is determined whether the state of prepared graphene is appropriate for use in a target device. A width of the closed curve may be in a range of, for example, 0.5 mm to 2 mm, but is not limited thereto. The width of the closed curve may be in a range of, for example, 1 to 100 mm$^2$, but is not limited thereto.

For example, when the growth coverage of graphene on a catalytic substrate is not uniform so that the catalytic substrate may have a portion in which graphene has not grown, an oxidation zone in which a catalytic layer between grain boundaries of graphene is oxidized and which is not in the form of a closed curve may be detectable.

For example, to determine the width of the closed curve, areas of closed curves are measured and an average and a standard deviation thereof are measured. When the standard deviation is in a range of 0 to 2, graphene may be determined as being appropriate for use.

FIG. 1 is a flowchart schematically illustrating a method of detecting a grain boundary of graphene, according to an embodiment of the present invention. Hereinafter, a method of detecting a grain boundary of graphene will be explained in connection with FIG. 1.

A stack of a catalytic metal and graphene is prepared (S1). In the preparing of the stack, graphene may be formed on at least a surface of a catalytic metal. Graphene may be formed by using various methods. For example, graphene may be formed by silver chemical vapor deposition (CVD), thermal chemical vapor deposition (TCVD), rapid thermal chemical vapor deposition (PTCVD), inductive coupled plasma chemical vapor deposition (ICP-CVD), or atomic layer deposition (ATLD). For example, graphene may be formed by CVD. The method of forming graphene is not limited thereto.

According to CVD, a vaporous carbon supplier is placed in a container with a catalytic metal located therein, and the container is heated and then cooled, thereby growing a graphene sheet on the surface of the catalytic metal.

The vaporous carbon supplier may be a carbon monoxide, ethane, ethylene, ethanol, acetylene, propane, butane, butadiene, pentane, pentene, cyclopentadiene, hexane, cyclohexane, benzene, toluene, or a mixture of these. At high temperature, the vaporous carbon supplier is divided into a carbon atom and a hydrogen atom. The separated carbon atom is deposited on a catalytic metal that has been heated, and then, the catalytic metal is cooled, thereby forming graphene.

The stack of the catalytic metal and graphene is reacted with an oxidizing solution (S2). The stack may be impregnated with the oxidizing solution, or the oxidizing solution may be coated on or sprayed onto the stack.

A grain boundary of graphene in the stack that has been reacted with the oxidizing solution is detected (S3). The grain boundary of the graphene may be detected by using an optical microscope.

By referring to the detected grain boundary of graphene, the state of graphene is determined (S4). In other words, the width, shape, and/or area distribution of the grain boundary of graphene are analyzed to determine whether graphene is defective.

Figure 4:
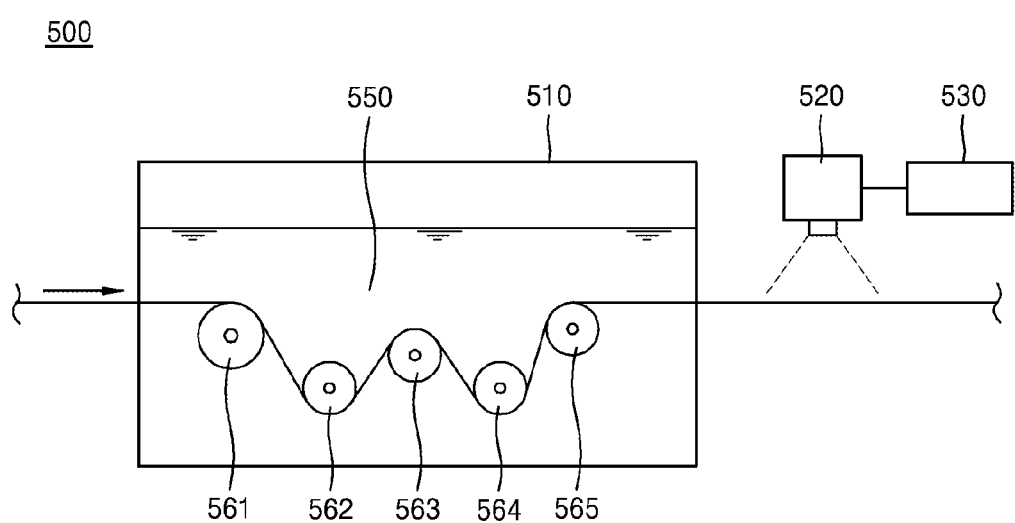
FIG. 4 is a schematic view of a device for detecting a grain boundary of graphene, according to an embodiment of the present invention.

FIG. 4 is a schematic view of a device 500 for detecting a grain boundary of graphene according to an embodiment of the present invention. Hereinafter, in connection with FIG. 4, the device 500 according to the present embodiment will be described.

Referring to FIG. 4, the device 500 includes a reactor 510, a detector 520, and a determination unit 530.

The reactor 510 reacts a stack of a catalytic metal and graphene with an oxidizing solution 550 to oxidize the catalytic metal. The structure of the reactor 510 is not limited as long as the stack is allowed to react with the oxidizing solution 550. When the stack is a flexible substrate, the stack may be reacted with the oxidizing solution 550 while being bent. Accordingly, the reactor 510 may have a smaller length or size.

The detector 520 detects the grain boundary of graphene. The detector 520 may not be any element that detects the grain boundary of graphene. For example, the detector 520 may be an optical microscope. The detector 520 may be connected to the reactor 510 in series. The stack that has reacted with the oxidizing solution 550 in the reactor 510 is transported to the detector 520, which then detects the grain boundary of graphene.

The determination unit 530 is connected to the detector 520, and receives and analyzes an optical microscopic image to determine the state of the graphene. How to determine the state of graphene is the same as described above and accordingly, descriptions therefor will be omitted herein.

The device 500 may further include a plurality of rollers. The rollers may be used to transport the stack of catalytic metal and graphene. When the stack of the catalytic metal and graphene is allowed to pass through the reactor 510 due to the rollers, the stack may react with the oxidizing solution 550.

Hereinbefore, in connection with FIGS. 1 and 4, a method of detecting a grain boundary of graphene according to an embodiment of the present invention, and a device for detecting a grain boundary of graphene according to an embodiment of the present invention have been described. However, the method of detecting a grain boundary of graphene and the device for detecting a grain boundary of graphene are not limited thereto.

Hereinafter, embodiments of the present invention will be described by referring to Examples. These examples are presented herein for illustrative purpose only and do not limit the scope of the present invention, which is obvious to one of ordinary skill in the art.

Example

A Cu plate having a thickness of 35 μm was loaded into a furnace for CVD. $CH_4$ was provided to the furnace at a temperature of about 1000° C. for about 10 minutes at a rate of 30 sccm. Then, in the $H_2$ atmosphere, the temperature was decreased to 600° C. at a speed of 80° C./min, and then, to room temperature at a speed of 40° C./min, thereby forming graphene on the Cu plate.

A stack of Cu and graphene was impregnated with 30 wt % of an aqueous hydrogen peroxide solution for 30 seconds.

Comparative Example

An experiment was performed in the same manner as in Example, except that the stack of Cu and graphene was not impregnated with an aqueous hydrogen peroxide solution.

Evaluation Example

Optical microscopic images of the stacks of Cu and graphene prepared according to Example and Comparative Example were obtained. An optical microscope used herein was Eclipse L200N manufactured by NIKON Corporation.

Figure 2:
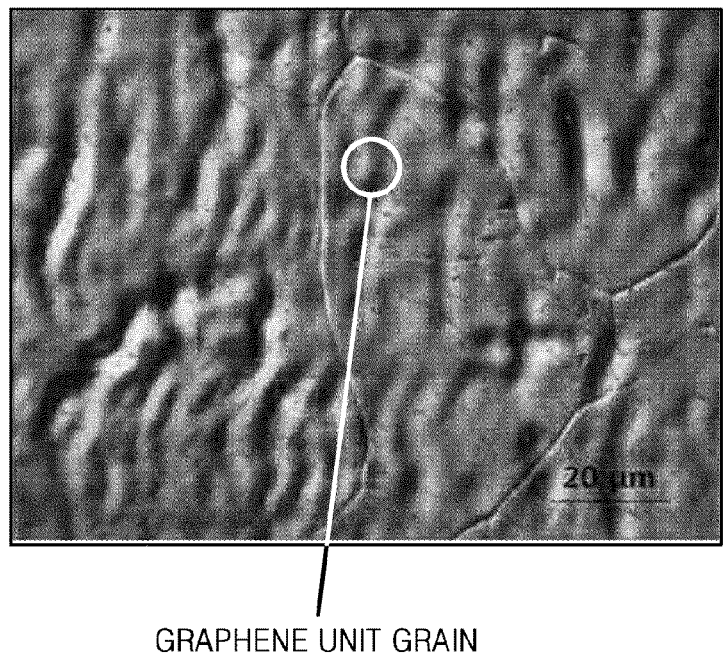
FIG. 2 shows an optical microscopic image of graphene that is treated by using the method of detecting a grain boundary of graphene according to an embodiment of the present invention.
Figure 3:
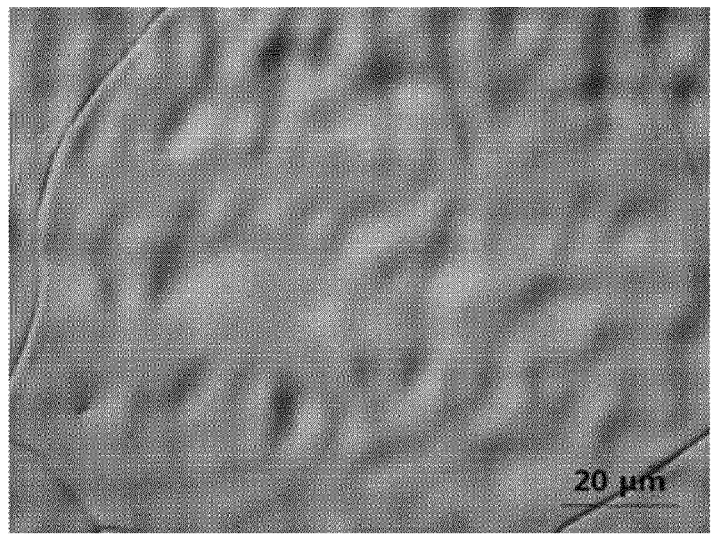
FIG. 3 shows an optical microscopic image of graphene prepared according to Comparative Example.

FIG. 2 shows an optical microscopic image of graphene prepared according to Example. FIG. 3 shows an optical microscopic image of graphene prepared according to Comparative Example.

Referring to FIG. 2, it is identified that when a stack of catalytic metal and graphene is reacted with an oxidizing solution, a grain boundary of graphene is detectable under optical microscope.

INDUSTRIAL APPLICABILITY

Embodiments of the present invention are applicable to a transparent electrode, an active layer, a display device including the same, an electronic device, a photoelectric device, a battery, a solar battery, or the like, each including graphene.

The invention claimed is:

1. A method of detecting a grain boundary of graphene, the method comprising oxidizing a catalytic metal by reacting a stack of the catalytic metal and graphene with 30 to 40 wt % of an aqueous hydrogen peroxide solution, wherein an amount of the aqueous hydrogen peroxide solution is in a range of 0.001 to 1 L based on 1 $m^2$ of a unit area of the stack of the catalytic metal and graphene, and wherein the aqueous hydrogen peroxide solution further comprises a dispersant, a stabilizer or a combination thereof in an amount of 1 to 15 wt % based on a total weight of the aqueous hydrogen peroxide solution.

2. The method of claim 1, wherein the catalytic metal comprises at least one selected from cobalt (Co), gold (Au), silver (Ag), aluminum (Al), chromium (Cr), magnesium (Mg), manganese (Mn), molybdenum (Mo), rhodium (Rh), silicon (Si), titanium (Ti), tungsten (W), uranium (U), vanadium (V), palladium (Pd), yttrium (Y), zirconium (Zr), germanium (Ge), and an alloy thereof.

3. The method of claim 1, wherein the catalytic metal is oxidized for 1 sec to 10 min.

* * * * *